(12) United States Patent
Antony

(10) Patent No.: US 9,623,061 B2
(45) Date of Patent: *Apr. 18, 2017

(54) **COMPOSITION OF EXTRACT OF *EMBLICA OFFICINALIS* AND METHOD OF PREPARING THE SAME**

(71) Applicant: Benny Antony, Ankamaly (IN)

(72) Inventor: Benny Antony, Ankamaly (IN)

(73) Assignee: ARJUNA NATURAL EXTRA as, LTD.

( * ) Notice: Subject to any disclaimer, the term of this patent is extended or adjusted under 35 U.S.C. 154(b) by 602 days.

This patent is subject to a terminal disclaimer.

(21) Appl. No.: 13/906,450

(22) Filed: May 31, 2013

(65) Prior Publication Data
US 2014/0093595 A1 Apr. 3, 2014

Related U.S. Application Data

(60) Continuation of application No. 13/261,098, filed as application No. PCT/IN2009/000460 on Aug. 20, 2009, now abandoned, application No. 13/906,450, which is a continuation-in-part of application No. 13/886,287, filed on May 3, 2013, now Pat. No. 8,945,634, which is a division of application No. 13/374,931, filed on Jan. 24, 2012, now Pat. No. 8,455,020, which is a division of application No. 12/805,191, filed on Jul. 16, 2010, now Pat. No. 8,158,167, which is a division of application No. 11/643,788, filed on Dec. 22, 2006, now Pat. No. 7,780,996, and a continuation-in-part of application No. 11/111,798, filed on Apr. 22, 2005, now abandoned, which is a continuation of application No. PCT/IN03/00137, filed on Apr. 3, 2003.

(30) Foreign Application Priority Data

Mar. 3, 2003 (IN) .................. 169/MAS/03
Jun. 29, 2009 (IN) .................. 1520/CHE/2009

(51) Int. Cl.
*A61K 36/185* (2006.01)
*A61K 36/47* (2006.01)

(52) U.S. Cl.
CPC ............ *A61K 36/185* (2013.01); *A61K 36/47* (2013.01)

(58) Field of Classification Search
CPC .................................................. A61K 36/185
USPC .................................................. 424/725, 776
See application file for complete search history.

(56) References Cited

U.S. PATENT DOCUMENTS

| 6,124,268 | A | 9/2000 | Ghosal |
| 6,235,721 | B1 | 5/2001 | Ghosal |
| 6,290,996 | B1 | 9/2001 | Ghosal |
| 6,362,167 | B1 | 3/2002 | Ghosal |
| 7,001,619 | B2 | 2/2006 | Johri et al. |
| 2003/0008045 | A1 | 1/2003 | Winston |
| 2003/0008048 | A1* | 1/2003 | Winston ............... A23L 1/3002 426/548 |
| 2003/0194452 | A1 | 10/2003 | Agarwal |

FOREIGN PATENT DOCUMENTS

WO WO 96/24327 A 8/1996
WO WO 02/23995 A 3/2002

OTHER PUBLICATIONS

Reza et al. "Effects of Emblica Officinalis (Amlaki) and Vitamin C on Cholesterol Induced Atherosclerosis in Rabbits", Journal Bangladesh College of Physicians and Surgeons, 1994 BD. 12(1): 3-7.*
Ghosal, S, Tripathi, VK and Chauhan S, Active Constituents of *Emblica Officinalis*: Part 1—The Chemistry and Antioxidative Effects of Two New Hydrolysable Tannins, Emblicanin A and B, Indian Journal of Chemistry, 35B: 941-948 (1996).
Anila, L., and Vijayalakshmi, NR, Flavonoids from *Emblica officinalis* and *Mangifera indica*—Effectiveness for Dyslipedemia, Journal of Ethnopharmacology, 79: 81-87 (2002).
Brewer, HB, High-Density Lipoproteins: A New Potential Therapeutic Target for the Prevention of Cardiovascular Disease, Arterioscler, Thromb. Vase. Biol. 24: 387-391 (2004).
Brewer, HB, Increasing HDI, Cholesterol Levels, N. Engl. J. Med., 350 (15): 1491-1494 (2004), Massachusetts Medical Society.
Furberg, CD, Adams, HP, Applegate, WB, Byington, RP, Espeland, MA, Hartwell, T, Hunninghake, DB, Lefkowitz, DS, Probstfield, J, and Riley, WA, Effect of Lovastatin on Early Carotid Artherosclerosis and Cardiovascular Events. Asymptomatic Carotid Artery Progression Study (ACAPS) Research Group, Circulation, 90: 1679-1687 (1994), American Heart Asociation.
Navab, M, Anantharamaiah, GM, Hama, S, Garber, DW, Chaddha, M, Hough, G, Lallone, R, and Fogelman, A, Oral Administration of an Apo A-1 Mimetic Peptide Synthesized From D-Amino Acids Dramatically Reduces Atherosclerosis in Mice Independent of Plasma Cholesterol, Circulation. 105: 290-292 (2002), American Heart Association.

(Continued)

*Primary Examiner* — Chris R Tate
*Assistant Examiner* — Deborah Davis
(74) *Attorney, Agent, or Firm* — Jyoti C Iyer

(57) ABSTRACT

The present disclosure relates to a composition of an extract of fruits of *Emblica officinalis* selected from the group consisting of liquid juice of fruits of *Emblica officinalis*, a powder of an alcoholic extract of fruits of *Emblica officinalis*, a powder of a hydro alcoholic extract of fruits of *Emblica officinalis*, a powder of a water extract of fruits of *Emblica officinalis*, a powder of a juice of fruits of *Emblica officinalis*, a powder of dried fruits of *Emblica officinalis*, a powder of a water extract of dried fruits of *Emblica officinalis*, a powder of a pectinase treated water extract of fruits of *Emblica officinalis*, and combinations thereof; a method of preparing such compositions of extract of fruits of *Emblica officinalis*, more particularly which has application as a nutraceutical or pharmaceutical for increasing HDL-C levels in patients with memory loss and dementia especially in patients with neurodegenerative diseases like Alzheimer's disease and for the treatment of memory loss especially in Alzheimer's disease.

10 Claims, No Drawings

(56) References Cited

OTHER PUBLICATIONS

Grundy, S, Statin Trials and Goals of Cindeslerol-Lowering Therapy, Circulation, 97: 1436-1439 (1998), American Heart Association.

Ridker, PM, Clinical Application of C-Reactive Protein for Cardiovascular Disease Detection and Prevention, Circulation, 107: 363-369 (2003), American Heart Association.

Ridker, P, Cannon, CP, Morrow, D, Rifai, N, Rose, LM, McCabe, Ch, Pfeffer, MA, and Braunwald, E. C-Reactive Protein Levels and Outcomes after Statin Therapy, N. Engl. J. Med., 352:20-28 (2005), Massachusetts Medical Society.

Chew, DP, Bhatt, DL, Robbins, MA, Penn, MS, Schneider, JP, Lauer, MS, Topol, EJ, and Ellis, SG, Incremental Prognostic Value of Elevated Baseline C-Reactive Protein Among Established Markers of Risk in Percutaneous Coronary Intervention, Circulation. 104: 992-997 (2001), America Heart Association.

Haffner, SM, Lehto, S, Ronnemaa, T, Pyorala, K, and Laakso, M, Mortality from Coronary Heart Disease in Subjects with Type 2 Diabetes and in Nondiabetic Subjects With and Without Prior Myocardial Infarction, N. Engl. J. Med., 339 (4): 229-234 (1998), Massachusetts, Medical Society.

Malmberg, K, Yusuf, S, Gerstein, HC, Brown, J, Zhao, F, Hunt, D, Piegas, L, Calvin, J, Keltai, M, Budaj, A, and for the OASIS Registry Investigators. Impact of Diabetes on Long-Term Prognosis in Patients with Unstable Angina and Non-Q-Wave Myocardial Infarction: Results of the OASIS (Organization to Assess Strategies for Ischemic Syndromes) Registry, Circulation, 102: 1014-1019 (2000), American Heart Association.

Sawin, CT, Geller, A, Wolf, PA, Belanger, AJ, Baker, E, Bachrach, P, Wilson, P. Benjamin, EJ, and D'Agostino RB, Low Serum Thyrotropin Concentrations as a Risk Factor for Atrial Fibrillation in Older Persons, N. Engl. J. Med., 331: 1249-1252 (1994).

Klein, I. and Ojamaa, K, Thyroid Hormone and the Cardiovascular System. N. Engl. J. Med., 344(7): 501-509 (2001), Massachusetts Medical Society.

Pasceri, V, Willerson, JT, and Yeh, ETH, Direct Proinflammatory Effect of C-Reactive Protein on Human Endothelial Cells, Circulation, 102: 2165-2168 (2000), American Heart Association.

Sacks, FM, Pfeffer, MA, Moye, LA, Rouleau, JL, Rutherford, JD, Cole, TG, Brown, L, Warnica, JW, Arnold, JMO, Wun, C-C, Davis, BR, and Braunwald, E, for the Cholesterol and Recurrent Events Trial Investigators, The Effect of Pravastatin on Coronary Events After Myocardial Infarction in Patients with Average Cholesterol Levels, N. Engl. J. Med., 335(14): 1001-1009 (1996), Massachusetts Medical Society.

Ross, R, Atherosclerosis—An Inflammatory Disease, N. Engl. J. Med., 340(2): 115-126 (1999), Massachusetts Medical Society.

Stefanick, ML, Mackey, S, Sheehan, M, Ellsworth, N, Haskell, WL, and Wood, PD, Effects of Diet and Exercise in Men and Postmenopausal Women with Low Levels of HDL Cholesterol and High Levels LDL Cholesterol, N. Engl. J. Med., 339(1): 12-20 (1998), Massachusetts Medical Society.

Pederson, TR, Olsson, AG, Faergeman, O, Kjekshus, J, Wedel, H, Berg, K, Wilhelmsen, L, Haghfelt, T, Thorgeirsson, G, Pyorala, K, Miettinen, T, Christophersen, B, Tobert, JA, Musliner, TA, Cook, TJ, for the Scandinavian Simvastatin Survival Study Group, Lipoprotein Changes and Reduction in the Incidence of Major Coronary Heart Disease Events in the Scandinavian Simvastatin Survival Study (4S), Circulation, 97: 1453-1460 (1998), American Heart Association.

Sacks, FM, Moye, LA, Davis, BR, Cole, TG, Rouleau, JL, Nash, DT, Pfeffer, MA, and Braunwald, E. Relationship Between Plasma LDL Concentrations During Treatment With Pravastatin and Recurrent Coronary Events in the Cholesterol and Recurrent Events Trial, Circulation, 97: 1446-1452 (1995), American Heart Association.

Ridker, PM, Rifai, N, Pfeffer, MA, Sacks, F, andBraunwald, E, Long-Term Effects of Pravastatin on Plasma Concentration of C-Reactive Protein, Circulation, 100:230-235 (1999), American Heart Association.

West of Scotland Coronary Prevention Study Group, Influence of Pravastatin and Plasma Lipids on Clinical Events in the West of Scotland Coronary Prevention Study (WOSCOPS) Circulation, 97: 1440-1445 (1998), American Heart Association.

Juonala, M, Viikari, JSA, Lattinen, T, Marniemi, J, Helenius, H, Ronnemaa, T, and Rattakari, OT, Interrelations Between Brachial Endothelial Function and Carotid Intima-Media Thickness in Young Adults: The Cardiovascular Risk in Young Finns Study, Circulation, 110: 2918-2923 (2004), American Heart Association.

Chen, Z, Fukutomi, T, Zago, AC, Ehlers, R, Detmers, PA, Wright, SD, Rogers, C, and Simon, DI, Simvastatin Reduces Neointimal Thickening in Low-Density Lipoprotein Receptor-Deficient Mice After Experimental Angioplasty Without Changing Plasma Lipids, Circulation, 106: 20-23 (2002), American Heart Association.

Sheperd, J, Cobbe, SM, Ford, I, Isles, CG, Lorimer, RA, MacFarlane, PW, McKillop, JH, and Packard, CJ, for the West of Scotland Coronary Prevention Study Group, Prevention of Coronary Heart Disease with Pravastatin in Men With Hypercholesterolmia, N. Engl. J. Med., 333(20): 1301-1307 (1995), Massachusetts Medical Society.

Thakur, CP, Thakur, B, Singh, S, Sinha, PK, and, Sinha, SK, The Ayurvedic medicines Haritaki, Amla and Bahira Reduce Cholesterol-Induced Atherosclerosis in Rabbits, Intl. J. Cardiology, 21: 167-175 (1988).

Thakur, CP, and Mandal, K, Effect of *Emblica officinalis* on Cholesterol-Induced Atherosclerosis in Rabbits, Indian J. Med. Res., 79 142-146 (1984), Indian Council of Medical Research.

Sai Ram, M, Neetu, D, Deepti, P, Vandana, M, Ilavazhagan, G, Kumar, D, and Selvamurthy, W, Cytoprotective Activity of Amla (*Emblica officinalis*) Against Chromium (VI) Induced Oxidative Injury in Murine Macrophages, Phytother. Res., 17: 430-433 (2003), John Wiley & Sons, Ltd.

Nemmani, KVS, Jena, GB, Dey, CS, Kaul, CL, and Ramarao, P, Cell Proliferation and Natural Killer Cell Activity by Polyherhal Formulation, Immu-21 in Mice, Indian Journal of Experimental Biology, 40: 282-287 (2002).

Panda, S, and Kar, A, Fruit Extract of *Emblica officinalis*Ameliorates Hyperthyroidism and Hepatic Lipid Peroxidation in Mice. Pharmazic. 58: 753-755 (2003).

Sabu, MC, and Kuttan, R, Anti-diabetic Activity of Medicinal Plants and its Relationship with their Antioxidant Property, J Ethnopharmacology 81: 155-160 (2002).

Sai Ram, M, Neetu, D, Yogesh, B, Anju, B, Dipti, P, Pauline, T, Sharma, SK, Sarada, SKS, Ilavazhagan, G, Kumar, D, and Selvamurthy, W, Cyto-protective and Immunomodulation Properties of Amla (*Emblica officinalis*) on Lymphocytes: An In-Vitro Study, J Ethnopharmacology, 81:5-10 (2002).

Muruganandam, AV, Kumar, V, and Bhattacharya, SK, Effect of Poly Herbal Formulation, EuMil on Chronic Stress-Induced Homeostatic Perurbations in Rats, Indian J Experimental Biology, 40: 1151-1160 (2002).

Babu, PS, and Prince, PSM, Antihyperglycaemic and Antioxidant Effect of Hyponidd, An Ayurvedic Herbomineral Formulation in Streptozotocin-Induced Diabetic Rats. J Pharmacy and Pharmacology, 56: 1435-1442 (2004).

Duan, W, Yu, Y, and Zhang, L, Antiatherogenic Effects of *Phyllanthus Emblica* Associated with Corilagin and its Analogue, Yakugaku Zasshi, 125(7); 587-591 (2005), The Pharmaceutical Society of Japan.

Tariq, M, Hussain, SJ, Asif, M, and Jahan, M, Protective Effect of Fruit Extracts of *Emblica officinalis* (Gaertn.) & *Terminalia belerica* (Roxb.) in Experimental Myocardial Necrosis in Rats, Indian J. exp. Biol., 15(6): 485-486 (1977).

Mishra, M, Pathhak, UN, and Khan, AB, *Emblica officinalis* Gaertn and Serum Cholesterol Level in Experimental Rabbits, Br. J. exp. Path., 62: 526-528 (1981).

Mathur, R, Sharma, A, Dixit, VP, and Varma, M, Hypolipidaemic Effect of Fruit Juice of *Emblica officinalis* in Cholesterol-Fed Rabbits, J. Ethnopharmacology, 50: 61-68 (1996), Elsevier Science Ireland Ltd.

Kim, HJ, Yokozawa, T, Kim, HY, Tohda, C, Rao, TP, and Juneja, LR, Influence of Amla (*Emblica officinalis* Gaertn.) on

(56) References Cited

OTHER PUBLICATIONS

Hypercholesterolemia and Lipid Peroxidation in Cholesterol-Fed Rats, J Nutr. Sci. Vitaminol, 51: 413-418 (2005).
Bhattacharya, A, Murganandam, AV, Kumar, V, and Bhattacharya, SK, Effect of Poly Herbal Formulation, EuMil. on Neurochemical Perturbations Induced by Chronic Stress, Indian J. exp. Biol., 40: 1161-1163 (2002).
Bhattacharya, SK, Bhattacharya, D, and Muruganandam, AV, Effects of *Emblica officinalis* Tannoids on a Rat Model of Tardive Dyskinesia, Indian J. exp. Biol., 38:945-947 (2000).
One page of International Search Report dated Dec. 1, 2003, from International Appl. No. PCT/IN03/00137.
Seven (7) pages of European Search Report dated Jun. 18, 2009.
Nalini D and Kapoor R, Effect of Plant Fruits: Indian Gall Nut, Bedda Nut and Gooseberry—On Hypercholesterolemic Rats, Plant Foods for Human Nutrition, 53(4):343-349 (1999).
Reza MS, Khan BR, Islam B, Muhsin AUM, and Quddus R, Effects of Emblica officinalis (amlaki) and Vitamin C on Cholesterol Induced Atherosclerosis in Rabbits, Journal of Bangladesh College of Physicians and Surgeons 1994 BD, 12(1):3-7 (1994).
Rader, DJ, High-density Lipoproteins and Atherosclerosis, American Journal of Cardiology, 90(8A) 62i-70i (2002).
Protest Documents filed by Third Party on Jul. 3, 2011, thirteen (13) pages.
Four (4) pages of International Search Report received in PCT/IN2009/000460 dated Apr. 13, 2010.
Beynen AC, Animal Models for Cholesterol Metabolism Studies, New Developments in Biosciences: The Implications for Laboratory Animal Science, Chapter 3, pp. 279-288 (1988), Springer Verlag.
Clay MA, Hopkins GJ, Ehnholm CP and Barter PJ, The rabbit as an animal model of hepatic lipase deficiency, Biochimica et Biophysica Acta, 1002: 173-181 (1989).
Connelly PW and Hegele RA, Hepatic lipase deficiency: Critical Reviews in Clinical Laboratory Sciences, 35(6):547-572 (1998).

\* cited by examiner

US 9,623,061 B2

COMPOSITION OF EXTRACT OF *EMBLICA OFFICINALIS* AND METHOD OF PREPARING THE SAME

This is a continuation of Ser. No. 13/261,098, filed Dec. 21, 2011, which is a 371 of PCT/IN2009/000460, filed Aug. 20, 2009, and a continuation-in-part of U.S. application Ser. No. 13/886,287, filed May 3, 2013, which is a Divisional of U.S. application Ser. No. 13/374,931, filed Jan. 24, 2012, which is a divisional of Ser. No. 12/805,191, filed Jul. 16, 2010, which is a Divisional of U.S. application Ser. No. 11/643,788, filed Dec. 22, 2006, which is a continuation of U.S. application Ser. No. 11/111,798, filed Apr. 22, 2005, which is a continuation of International Application PCT/IN2003/000137, with an international filing date of Apr. 3, 2003 and claiming priority of India Patent Application 169/MAS/2003 filed on Mar. 3, 2003, which documents are all incorporated herein by reference.

FIELD OF THE INVENTION

The present disclosure relates to a composition of the extract of fruits of *Emblica officinalis*, a method of preparing a composition consisting of extract of fruits of *Emblica officinalis* more particularly which has application as a nutraceutical or pharmaceutical for increasing HDL-C levels in patients with memory loss and dementia especially in patients with neurodegenerative diseases like Alzheimer's disease and for the treatment of memory loss, dementia especially in Alzheimer's disease.

DESCRIPTION OF RELATED ART

In our everyday life almost all the activities in one way or other deal with memory. Loss of memory means loss of one's self. Learning will make no sense if it is not retained by the individual. It is only through memory that we are able to relate different events, experiences, conditions, people, objects etc. Memory is needed in making social relationships, mastering cognitive competencies (mental capacities) and solving various problems.

Memory is a remarkable process and system which receives information from both external and internal stimuli, retains it and makes it available on future occasion. The retrieval of information can be in the same way or in a different form and the reception depends on the information we already have. We neither receive nor retain all the information presented to us because there is a great deal of selectivity in receiving the information. Human memory can retain extremely large amount of information. It is an active system which can integrate, add, modify, omit or reorganize the information.

Since first addressed by Kral (1) in the late 1950s, numerous studies (2, 3, 4, 5, 6, 7, 8) have documented poorer memory performance in older compared with younger age groups. Although the exact prevalence is uncertain, most agree that memory decline occurs in more than 40% of individuals older than 60 years. (9) Despite this high prevalence, or perhaps because of it, there is continued debate about whether memory decline in otherwise healthy older people should be considered a clinical entity. Studies, (10) with humans and animals have shown that memory decline is not inevitable with increasing age and therefore should be considered a clinical entity.

The number and proportion of aging individuals in the population is increasing. These aging individuals expect to lead intellectually challenging lives in an environment rich with information and reliant on rapidly changing technologies. The ability to negotiate this environment depends on cognitive skills that include the specific types of memory systems most vulnerable to age-associated changes. Memory decline interferes with an aging individual's activities of daily living, without necessarily progressing to amnesia or extending into dementia (11, 12, 13).

Because Alzheimer's disease (AD) is relatively common in individuals older than 65 years and because AD pathological processes target the hippocampal formation early in its course, (14) early AD is a major contributor to memory decline in otherwise healthy and nondemented older people. Still, not every older individual with memory deficits progresses to AD dementia. (15, 16)

Currently, there are an estimated 24 million people worldwide with dementia. Two thirds of them live in developing countries. This figure is set to increase to more than 80 million by 2040. Much of this increase will be in rapidly developing and heavily populated regions such as China, India, and Latin America. Alzheimer's disease is by far the commonest cause of dementia in the elderly, being responsible for 65-80 percent of dementia cases (17, 18).

Alzheimer's disease (AD) is a neurodegenerative disorder that results in progressive loss of memory, changes in personality, and cognitive decline. The UN population projections estimate that the number of people older than 80 years will approach 370 million by the year 2050. Currently, it is estimated that 50% of the people over the age of 85 years are afflicted with AD. Therefore, by 2050, more than 100 million people worldwide are likely to suffer from this devastating disease.

One in eight men and almost one in four women will develop Alzheimer's disease during their lifetime. In a population-based study of people older than age 65 years, dementia was the strongest risk factor for mortality, surpassing heart disease, stroke, diabetes, and cancer (19).

The vast number of people requiring constant care and other services can severely strain medical, monetary and human resources. An effective, disease-modifying treatment of Alzheimer's disease remains an unmet need of modern medicine. The dementia of AD has an insidious onset and a gradually progressive course. Although the pathogenesis of the disease remains unclear, the process is widely thought to begin in midlife or earlier, decades before the appearance of symptoms.

The extent and complexity of Alzheimer's disease that affects numerous cells, molecules, systems and pathways, impede attempts to determine which changes are specifically associated with early pathology. Consequently, a number of hypotheses exist, and a number of treatment options are also suggested. The patient, in the meantime, remains at the mercy of the proponents of these hypotheses. Most of the clinical trials have returned negative results. Nearly 50,000 research reports have been published on AD, yet we aren't anywhere near a disease-modifying treatment option which simultaneously addresses the various facets of the disease. Current approaches and proposals address one single aspect and the disappointing results largely arise because of this basic flaw.

A disease-modifying treatment regimen for Alzheimer's disease is an urgent need. Before this can be achieved, we need to understand the mechanism of the disease itself. Various treatment options presently suggested and followed are without clear understanding of the disease process itself, and quite expectedly, all have failed at the clinic.

Despite a previous sharp distinction between vascular and neurodegenerative diseases, evidence linking vascular risk factors and indicators of vascular disease to Alzheimer's disease has accumulated over the past decade. In particular, evidence is growing for a possible association between lipids and Alzheimer's disease or dementia.

The central nervous system is a lipid-rich organ, and approximately 25 percent of the total amount of cholesterol present in humans is localized in the brain and the central nervous system, mainly in the myelin sheath (i.e., oligodendroglia) and the membranes of astrocytes and neurons (20, 21). Lipoprotein complexes are critical for synaptic maturation and maintenance of synaptic plasticity (22, 23) and synaptic growth, regeneration, and neuritic outgrowth depend greatly on the availability of brain lipids (22, 23, 24).

Evidence is growing that lipid-rich membrane microdomains are involved in regulating the trafficking and amyloidogenic processing of amyloid precursor protein (25). Binding of β-amyloid to lipids may play an important role in maintaining the peptide in solution and thus be particularly relevant to β-amyloid's normal and pathologic biochemistry and physiology (26). Elevated dietary cholesterol has been shown to increase amyloid plaque formation in different in vivo models (27, 28), and cholesterol loading and cholesterol depletion have also been shown to affect β-amyloid generation, (29). Dietary cholesterol could induce Alzheimer-like β-amyloid immunoreactivity in rabbit brains (28), and disruption of cholesterol homeostasis in Alzheimer's disease has been linked to β-amyloid pathology (30).

High density lipoprotein (HDL) cholesterol prevents aggregation and polymerization of β-amyloid (26). HDL cholesterol may also influence dementia risk through its anti inflammatory (31) and antioxidant (32) effects. In cross-sectional studies, lower HDL cholesterol levels have been associated with lower Mini-Mental State Examination scores (33) and with higher dementia (33, 34, and 35) and Alzheimer's disease (36) risks.

The associations between midlife lipid levels and late life dementia appear to be robust (37 . . . 40). However, the precise lipid that might be important remains unclear, with studies implicating high levels of LDL-C, (41, 42) or total cholesterol (TC) (37-39, 43) or low levels of high-density lipoprotein cholesterol (HDL-C) (44-50). HDL-C is critical for the maturation of synapses and the maintenance of synaptic plasticity (51). It can influence the formation of amyloid, the main constituent of amyloid plaques (52). Low HDL-C has also been shown to be associated with lower hippocampal volume (21).

A low level of HDL-C is a risk factor for cardiovascular disease. Recent studies suggest a robust association between low level of High Density Lipoprotein-Cholesterol (HDL-C)<40 mg/dL and poor memory. The Whitehall II study, (53) showed that association of low level of HDL-C with memory was independent of other lipids and identified HDL-C as being important for memory. There are different mechanisms connecting low levels of HDL-C and memory as HDL-C is a prominent lipoprotein in the human brain. It is involved in the regulation of amyloid beta protein metabolism and deposition in the brain. Deficit in HDL-C could affect memory through its influence on atherosclerotic disease and stroke. The linking of HDL-C to neurodegenerative diseases also involves its anti inflammatory or anti oxidant properties.

The supplementation of extract of fruits of Emblica officinalis has shown to increase the levels of HDL-C as well as decrease the levels of LDL-C and total cholesterol. The beneficial effect is documented in animal and human clinical studies (54-56). Since memory loss is linked with low levels of HDL-C, supplementation of extract of fruits of Emblica officinalis will have beneficial effect in increasing levels of HDL-C and improving memory. Memory deficit is critical to the diagnosis of cognitive impairment and Alzheimer's disease.

The present disclosure gives a composition of extracts of fruits of Emblica officinalis, a method of preparation of the said compositions of extract of fruits of Emblica officinalis and method of supplementing to patients with low HDL-C level, memory loss and dementia especially in patients with Alzheimer's disease giving therapeutically beneficial effect by increasing the level of HDL-C and improving the memory and cognition and for the treatment of Alzheimer's disease.

OBJECT OF THE INVENTION

The object of the invention is to provide a composition of the extracts of fruits of Emblica officinalis which has an application as a nutraceutical or pharmaceutical for increasing HDL-C levels in patients with memory loss and dementia especially in patients with neurodegenerative diseases like Alzheimer's disease and for the treatment of memory loss, dementia especially in Alzheimer's disease.

Another object of the present invention is to provide a method of preparing a composition of the extracts of fruits of Emblica officinalis which has an application as a nutraceutical or pharmaceutical for increasing HDL-C levels in patients with memory loss and dementia especially in patients with neurodegenerative diseases like Alzheimer's disease and for the treatment of memory loss, dementia especially in Alzheimer's disease.

Yet other object of the invention is to provide a method of supplementing the composition to the patients with low HDL-C level, memory loss and dementia especially in patients with Alzheimer's disease giving therapeutically beneficial effect by increasing the level of HDL-C and improving the memory loss and dementia especially in patients with neurodegenerative diseases like Alzheimer's disease and for the treatment of memory loss, dementia especially in Alzheimer's disease.

SUMMARY OF THE INVENTION

The present invention relates to a composition of the extract of fruits Emblica officinalis consisting of liquid juice of fruits of Emblica officinalis, a powder of an alcoholic extract of fruits of Emblica officinalis, a powder of a hydro alcoholic extract of fruits of Emblica officinalis, a powder of a water extract of fruits of Emblica officinalis, a powder of a juice of fruits of Emblica officinalis, a powder of dried fruits of Emblica officinalis, a powder of a water extract of dried fruits of Emblica officinalis, and, a powder of a pectinase treated water extract of fruits of Emblica officinalis, a method of preparing such compositions of extract of fruits of Emblica officinalis, more particularly which has application as a nutraceutical or pharmaceutical for increasing HDL-C levels in patients with memory loss and dementia especially in patients with neurodegenarative diseases like Alzheimer's disease and for the treatment of memory loss, dementia especially in Alzheimer's disease.

DETAILED DESCRIPTION

Human studies show that low level of HDL-C is associated with poor memory and decline in HDL-C is associated with decline in memory over a 5 year period. Cognitive impairment is a key feature of neurodegenerative diseases like Alzheimer's disease. A method to increase the HDL-C can improve the cognitive functions and can offer a new approach to treat patients with neurodegenerative diseases with memory loss or dementia especially Alzheimer's disease. It may also offer a new method to prevent the impairment in cognitive functions especially memory.

The present disclosure provides a composition of the extract of fruits of *Emblica officinalis*, a method of preparing extract of fruits of *Emblica officinalis* more particularly which has application as a nutraceutical or pharmaceutical for increasing HDL-C levels in patients with memory loss and dementia especially in patients with neurodegenerative diseases like Alzheimer's disease and for the treatment of memory loss, dementia especially in Alzheimer's disease.

Some embodiments of the extract of fruits of *Emblica officinalis* include a liquid juice of fruits of *Emblica officinalis*, a powder of an alcoholic extract of fruits of *Emblica officinalis*, a powder of a hydroalcoholic extract of fruits of *Emblica officinalis*, a powder of a water extract of fruits of *Emblica officinalis*, a powder of a juice of fruits of *Emblica officinalis*, a powder of dried fruits of *Emblica officinalis*, a powder of a water extract of dried fruits of *Emblica officinalis*, and, a powder of a pectinase treated water extract of fruits of *Emblica officinalis*, and combinations thereof.

The different extracts of fruits of *Emblica officinalis* are likely to differ in constituents. In some embodiments, a liquid juice of fruits of *Emblica officinalis* can include polyphenols, hydrolysable galloellagitannins, soluble and insoluble fiber, starch, sugar and carbohydrates. In some embodiments, a powder of an alcoholic extract of fruits of *Emblica officinalis* can include soluble fiber, soluble resin, fat and polyphenolic compounds present in the fruits of *Emblica officinalis* including hydrolysable galloellagitannins. In some embodiments, a powder of a hydroalcoholic extract of fruits of *Emblica officinalis* can include water soluble polyphenols, hydrolysable galloellagi tannins, soluble sugar and fiber. In some embodiments, a powder of a water extract of fruits of *Emblica officinalis* can include soluble polyphenols, hydrolysable galloellagi tannins, soluble fiber, carbohydrate and starch. In some embodiments, a powder of a juice of fruits of *Emblica officinalis* can include polyphenols, hydrolysable galloellagi tannins, soluble and insoluble fiber, starch, carbohydrate and sugar. In some embodiments, a powder of dried fruits of *Emblica officinalis* can include soluble and insoluble fiber, fat, sugar, organic acids like oxalic acids and polyphenolic compounds present in the fruits of *Emblica officinalis* including hydrolysable galloellagitannins. In some embodiments, a powder of a water extract of dried fruits of *Emblica officinalis* can include water soluble polyphenols, hydrolysable galloellagi tannins, soluble fiber, carbohydrate and starch. In some embodiments, a powder of a pectinase treated water extract of fruits of *Emblica officinalis* can include polyphenols, galloellagi tannins, simple sugars and soluble fibers.

In some embodiments, an extract of the fruits of *Emblica officinalis* can be provided in a dosage form selected from the group consisting of capsule, tablet, granule, sachet, powder, paste, ointment, infusion, injection, ampoule, solution, suspension, emulsion, pill, sustained release formulation and combinations thereof. An extract of the fruits of *Emblica officinalis* includes embodiments, such as, a liquid juice of fruits of *Emblica officinalis*, a powder of an alcoholic extract of fruits of *Emblica officinalis*, a powder of a hydroalcoholic extract of fruits of *Emblica officinalis*, a powder of a water extract of fruits of *Emblica officinalis*, a powder of a juice of fruits of *Emblica officinalis*, a powder of dried fruits of *Emblica officinalis*, a powder of a water extract of dried fruits of *Emblica officinalis*, a powder of a pectinase treated water extract of fruits of *Emblica officinalis*, and combinations thereof.

In some embodiments, the extract of fruits of *Emblica officinalis* includes about 12% to 70% polyphenols. In some embodiments, the extract of fruits of *Emblica officinalis* includes about 5% to about 35% hydrolysable gallo ellagic tannins.

In one embodiment of the method of preparing a powder of an alcoholic extract of fruits of *Emblica officinalis*, fresh fruits of *Emblica officinalis* having moisture 90% are pulverized and charged into an extractor. 95% methyl alcohol is pumped into the extractor and incubated. Then the solvent part is collected and fresh alcohol pumped again into the extractor. The extraction can be repeated thrice. All the extracts are pooled, filtered and dried in an Agitated thin film drier (ATFD) under a vacuum of about 700 mm Mercury. Dried product is discharged from the bottom of the vessel, pulverized and sieved through 30 mesh to obtain a powder of an alcoholic extract of fruits of *Emblica officinalis*. In some embodiments, the polyphenol content of the alcoholic extract can range from about 40% to about 70% by weight of the extract. In some embodiments, the hydrolysable gallo ellagic tannins can range from about 25% to about 35% by weight of the extract.

In one embodiment of the method of manufacture of a powder of a hydroalcoholic extract of fruits of *Emblica officinalis*, fresh fruits of *Emblica officinalis* are pulverized and charged into an extractor. Alcohol (methyl alcohol) water mixture (70:30) is pumped into the extractor and kept for a contact time of 3 hrs. Then the solvent part is collected and the fresh solvent pumped again into extractor and repeated thrice. All the extracts are pooled, filtered and concentrated in an Agitated thin film evaporator (ATFE). Then the concentrate is fed into vacuum stripper and dried under vacuum at above 500 mm of mercury. Dried product is discharged from the bottom of the vessel then pulverized and sieved through 30 mesh to obtain the dried hydro alcoholic powder of fruits of *Emblica officinalis*. In some embodiments, the polyphenol content of the extract ranges by weight from about 35% to about 65% by weight of the extract. In some embodiments, the hydrolysable galloellagic tannins range from about 25% to about 35% by weight of the extract.

In one embodiment of the method of manufacture of a powder of water extract of fruits of *Emblica officinalis*, fresh fruits of *Emblica officinalis* are pulverized and charged into an extractor. Water is pumped into the extractor and kept for a contact time of 3 hrs. Then the solvent part is collected and the fresh solvent pumped again into extractor and repeated thrice. All the extracts are pooled, filtered and concentrated in an evaporator. When the concentrate reaches the bottom of the vessel, the concentrate is fed into drier and dried under vacuum above 500 mm of mercury. Dried product is discharged from the bottom of the vessel, then pulverized and sieved through 30 mesh to obtain the powder of water extract of fruits of *Emblica officinalis*. In some embodiments, the polyphenol content of the extract ranges from about 35% to about 65% by weight of the extract. In some embodiments, the hydrolysable gallo ellagin tannins ranges from about 18% to about 35% by weight of the extract.

In one embodiment of the method of manufacture of a powder of juice of fruits of *Emblica officinalis*, fresh fruits of *Emblica officinalis* are collected and washed with water. The cleaned fruits are crushed in the screw expeller. The initial juice obtained on the tray of the screw expeller is collected in the feed tank under room temperature of 27° C. The initial juice is centrifuged to obtain filtrate which is collected and the residue which is removed. The collected filtrate is clarified in a rotating disc type clarifier (RPM-18000) to obtain final filtrate and some residue. After removing the residue, the final filtrate (clarified juice of Amla) is collected. This is dried in a spray drier which is set at inlet temperature 180° C. and outlet temperature 90° C., which is sieved through 30 mesh, to obtain a powder of juice of fruits of *Emblica officinalis*. In some embodiments, the polyphenol content ranges from about 35% to about 65% by weight of the extract. In some embodiments, the hydrolysable gallo ellagic tannins content ranges from about 20% to about 35% by weight of the extract.

In one embodiment of the method of manufacture of a powder of dried fruits of *Emblica officinalis*, fresh fruits of *Emblica officinalis* are collected and washed with water, chopped into flakes and dried in a hot air oven at around 110° C. for 10 hours. The dried material is powdered, sterilized under controlled temperature and passed through 30 mesh sieve to obtain powder of juice of fruits of *Emblica officinalis*. In some embodiments, the polyphenol content ranges form about 12% to about 30% by weight of the extract. In some embodiments, the hydrolysable gallo ellagic tannins ranges from about 5-20% by weight of the extract.

In one embodiment of the method of manufacture of a powder of a water extract of dried fruits of *Emblica officinalis*, fresh fruits of *Emblica officinalis* are collected and washed with water, chopped into flakes and dried in a hot air oven at around 110° C. for 10 hours. Water is added into the dried flakes and kept for a contact time of 3 hrs. Then the solvent part is collected and the fresh solvent pumped again into dried flakes and repeated thrice. All the extracts are pooled, filtered and concentrated in an evaporator, when the concentrate reaches the bottom of the vessel; the concentrate is fed into drier and dried under vacuum above 500 mm of mercury. Dried product is discharged from the bottom of the vessel, then pulverized and sieved through 30 mesh to obtain a powder of a water extract of dried fruits of *Emblica officinalis*. In some embodiments, the polyphenol content ranges from about 30% to about 60% by weight of the extract. In some embodiments, the hydrolysable gallo ellagic tannins range from about 8% to about 25% by weight of the extract.

In one embodiment of method of manufacture of liquid juice of fruits of *Emblica officinalis*, fresh fruits of *Emblica officinalis* are collected, and washed with water. The cleaned fruits are crushed in the screw expeller. The initial juice obtained on the tray of the screw expeller is collected in the feed tank under room temperature of 27° C. The initial juice is centrifuged to obtain filtrate which is collected and the residue which is removed. The collected filtrate is clarified in a rotating disc type clarifier (RPM-18000) to obtain final filtrate and some residue. After removing the residue, the final filtrate (liquid juice of fruits of *Emblica officinalis*) is collected. In some embodiments, the polyphenol content ranges from about 12% to about 14% by weight of the extract. In some embodiments, the hydrolysable gallo ellagic tannins range from about 5% to about 7% by weight of the extract.

In one embodiment of the method of manufacture of a powder of a pectinase treated water extract of fruits of *Emblica officinalis* is by pulping fruits of *Emblica officinalis* with demineralized water to create slurry. The slurry is treated with pectinase and then filtered to obtain a solution. The solution is concentrated and dried under vacuum. Dried product is pulverized and sieved through 30 mesh to obtain a powder of the pectinase treated water extract of fruits of *Emblica officinalis*. In some embodiments the polyphenol content of the extract ranges from about 35% to about 65% by weight of the extract. In some embodiments, the hydrolysable gallo ellagic tannins range from about 16% to about 35% by weight of the extract.

In some embodiments, capsules having the extract of *Emblica officinalis* are prepared. A 500 mg capsule containing 500 mg of a powder of extract of fruits of *Emblica officinalis* is prepared by encapsulating the powder in hard gelatin capsules. The process is performed in an air-conditioned at 21° C. and de-humidified room. The extract powder is charged into the hopper of a semi-automatic capsule filling machine. '0' size hard gelatin capsule shell is loaded to the tray and the extract powder is filled into the shell. The filled weight of capsules are checked simultaneously and these capsules are sorted by a sorting machine and polished with the help of a polishing machine to give capsules of 500 mg each.

A 250 mg capsule containing 250 mg powder of extract of fruits of *Emblica officinalis* can be prepared by encapsulating the powder in hard gelatin capsules. The process is performed in an air-conditioned at 21° C. and de-humidified room. The extract powder is charged into the hopper of a semi-automatic capsule filling machine. '2' size hard gelatin capsule shell is loaded to the tray and the extract powder is filled into the shell. The filled weight of capsules are checked simultaneously and these capsules are sorted by a sorting machine and polished with the help of a polishing machine to give capsules of 250 mg each.

In some embodiments, an extract of fruits of *Emblica officinalis* can be administered at a dose of 500 mg capsules once daily for 4 months. Administration of 500 mg capsules of extract of fruits of *Emblica officinalis* including a liquid juice of fruits of *Emblica officinalis*, a powder of an alcoholic extract of fruits of *Emblica officinalis*, a powder of a hydroalcoholic extract of fruits of *Emblica officinalis*, a powder of a water extract of fruits of *Emblica officinalis*, a powder of a juice of fruits of *Emblica officinalis*, a powder of dried fruits of *Emblica officinalis*, a powder of a water extract of dried fruits of *Emblica officinalis*, and, a powder of a pectinase treated water extract of fruits of *Emblica officinalis* once daily for 4 months to patients having low levels of HDL-C (below 40 mg/dL) resulted in an increase in the HDL-C level. Normal healthy subjects having HDL-C below 40 mg/dL given 500 mg capsules of each of the above mentioned extracts daily at night for 4 months showed an increase in HDL-C levels with the powder of juice of fruits of *Emblica officinalis* showing a maximum increase of 20% in HDL-C levels compared to placebo as seen in table: 1.

Administration of the extract of fruits of *Emblica officinalis* include a liquid juice of fruits of *Emblica officinalis*, a powder of an alcoholic extract of fruits of *Emblica officinalis*, a powder of a hydroalcoholic extract of fruits of *Emblica officinalis*, a powder of a water extract of fruits of *Emblica officinalis*, a powder of a juice of fruits of *Emblica officinalis*, a powder of dried fruits of *Emblica officinalis*, a powder of a water extract of dried fruits of *Emblica officinalis*, and, a powder of a pectinase treated water extract of fruits of *Emblica officinalis* resulted in increased HDL-C level and improved memory in patients with HDL-C below 40 mg/dL and having associated memory loss. As seen in Table 2, subjects having HDL-C levels below 40 mg/dL and short term memory loss given 250 mg capsules of the different extracts of fruits of *Emblica officinalis* twice daily for a period of 6 months showed an increase in HDL-C levels and an increase in memory as seen in Table 2. Among the different extracts, powder of water extract of fruits of *Emblica officinalis* is the most significant with a 25.7% increase in HDL-C levels and 30% increase in memory levels as seen in table: 2.

In some embodiments, administration of an extract of fruits of *Emblica officinalis*, including a powder of an alcoholic extract of fruits of *Emblica officinalis*, a powder of a water extract of *Emblica officinalis*, a powder of a hydroalcoholic extract of fruits of *Emblica officinalis*, a powder of a water extract of dried fruits of *Emblica officinalis*, or, a powder of a pectinase treated water extract of fruits of *Emblica officinalis*, 250 mg capsules twice daily for 6 months in patients with HDL-C is <40 mg/dl and MMSE score in the range 10 to 26 and 6CIT score of more than 8, resulted in an increased HDL-C level along with improvement in dementia as seen in table: 3. Of the different extracts of fruits of *Emblica officinalis* at a dose of 250 mg capsules twice daily for 6 months most significant improvement in the HDL-C level is seen in group of patients given powder or a water extract of *Emblica officinalis*. This increase also correlated with significant improvement in dementia assessed by MMSE and 6CIT scoring in the same group as seen in table: 3.

In some embodiments, administration of the extract of fruits of *Emblica officinalis* include a liquid juice of fruits of *Emblica officinalis*, a powder of an alcoholic extract of fruits of *Emblica officinalis*, a powder of a hydroalcoholic extract of fruits of *Emblica officinalis*, a powder of a water extract of fruits of *Emblica officinalis*, a powder of a juice of fruits of *Emblica officinalis*, a powder of dried fruits of *Emblica officinalis*, a powder of a water extract of dried fruits of *Emblica officinalis*, and, a powder of a pectinase treated water extract of fruits of *Emblica officinalis* inpatients with low levels of HDL-C (below 40 mg/dL) and probable Alzheimer's disease with the presence of mild to moderate dementia resulted in an increased HDL-C level along with improvement in cognition as seen in Table 4. Patients given alcoholic extracts of fruits of *Emblica officinalis* in a dose of 250 mg twice daily for 6 months showed maximum increase in HDL-C level which correlated with similar improvement in ADAS-cog scores compared to placebo as seen in table: 4. This signifies that the increase in HDL-C level is associated with improvement in the cognitive symptoms. It offers a new method of treating patients with Alzheimers disease.

It will be readily understood by the skilled artisan that numerous alterations may be made to the examples and instructions given herein. These and other objects and features of present invention will be made apparent from the following examples. The following examples as described are not intended to be construed as limiting the scope of the present invention.

Example 1

Method of Manufacture of a Powder of an Alcoholic Extract of Fruits of *Emblica officinalis*

Fresh fruits of *Emblica officinalis* (100 kilograms) having moisture 90% was pulverized and charged into an extractor. Around 200 liters of 95% methyl alcohol was pumped into the extractor and kept for a contact time of 3 hours. Then the solvent part was collected and fresh methyl alcohol pumped again into the extractor and extraction repeated thrice. All the extracts were pooled, filtered and dried in an Agitated thin film drier (ATFD) which is working under vacuum 700 mm Mercury. Dried product (5 Kg) was discharged from the bottom of the vessel then pulverized and sieved through 30 mesh to obtain of powder of an alcoholic extract of fruits of *Emblica officinalis*.

The powder of the alcoholic extract of fruits of *Emblica officinalis* was found to have the following composition.
Polyphenol content: 70% (Titration method)
Hydrolysable gallo ellagictannins: 35% (HPTLC method)

Example 2

Method of Manufacture of a Powder of a Hydroalcoholic Extract of Fruits of *Emblica officinalis*

Fresh fruits of *Emblica officinalis* 100 kgs was pulverized and charged into an extractor. Around 200 liters of methyl alcohol water mixture (70:30) was pumped into the extractor and kept for a contact time of 3 hrs. Then the solvent part collected and the fresh solvent pumped again into extractor and repeated thrice. All the extracts were pooled, filtered and concentrated in an Agitated thin film evaporator (ATFE) to TDS 30.0% (Total dissolved solids). Then the concentrate was fed into vacuum stripper and dried under vacuum at above 500 mm of mercury. Dried product (5 kg) is discharged from the bottom of the vessel, then pulverized and sieved through 30 mesh to obtain a powder of hydro alcoholic extract of fruits of *Emblica officinalis*.

The powder of the hydro alcoholic extract of fruits of *Emblica officinalis* was found to have the following composition.
Polyphenol content: 65% (Titration method)
Hydrolysable gallo ellagic tannins: 35% (HPTLC method)

Example 3

Method of Manufacture of a Powder of a Water Extract of Fruits of *Emblica officinalis*

Fresh fruits of *Emblica officinalis* 100 kgs was pulverized and charged into an extractor. Around 200 Liters of water was pumped into the extractor and kept for a contact time of 3 hrs. Then the solvent part was collected and the fresh solvent pumped again into extractor and repeated thrice. All the extracts were pooled, filtered and concentrated in an evaporator, when the concentrate reaches the bottom of the vessel; the concentrate is fed into drier and dried under vacuum above 500 mm of mercury. Dried product (6 Kg) was discharged from the bottom of the vessel, then pulverized and sieved through 30 mesh to obtain a powder of a water extract of fruits of *Emblica officinalis*.

The powder of the water extract of fruits of *Emblica officinalis* was found to have the following composition.
Polyphenol content: 60% (Titration method)
Hydrolysable gallo ellagic tannins: 25% (HPTLC method)

Example 4

Method of Manufacture of Powder of Juice of Fruits of *Emblica officinalis*

Fresh fruits of *Emblica officinalis* 100 kgs was collected, and washed with water. The cleaned fruits were crushed in the screw expeller. The initial juice obtained on the tray of the screw expeller was collected in the feed tank under room temperature of 27° C. The initial juice was centrifuged to obtain filtrate which was collected and the residue which was removed. The collected filtrate was clarified in a rotating disc type clarifier (RPM-18000) to obtain a final filtrate and some residue. After removing the residue, the final filtrate (clarified juice of *Emblica officinalis*) was collected with a yield 60-70% of fruits of *Emblica officinalis* with total dissolved solids (TDS) 4-7%. The final filtrate was dried in a spray drier set at inlet temperature 180° C. and outlet temperature 90° C. Around 3 kgs of product was obtained which was sieved through 30 mesh, to obtain the powder of a juice of fruits of *Emblica officinalis*.
The powder of the juice of fruits of *Emblica officinalis* was found to have the following composition.
Polyphenol content: 62% (Titration method)
Hydrolysable gallo ellagic tannins: 30% (HPTLC method)

Example 5

Method of Manufacture of Powder of Dried Fruits of *Emblica officinalis*

Fresh fruits of *Emblica officinalis* 100 kgs were washed and chopped into flakes and dried in a hot air oven at around 110° C. for 10 hours. The dried material (9 kgs) was powdered, sterilized under controlled temperature and passed through a 30 mesh sieve to obtain a powder of dried fruits of *Emblica officinalis*.
The powder of dried fruits of *Emblica officinalis* was found to have the following composition.
Polyphenol content: 20% (Titration method)
Hydrolysable gallo ellagic tannins: 12% (HPTLC method)

Example 6

Method of Manufacture of Powder of a Water Extract of Dried Fruits of *Emblica officinalis*

Fresh fruits of *Emblica officinalis* 100 kgs was washed and chopped into flakes and dried in a hot air oven at around 110° C. for 10 hours. Around 200 Liters of water was added into the dried flakes and kept for a contact time of 3 hrs. Then the solvent part was collected and the fresh solvent was again added into flakes and repeated thrice. All the extracts were pooled, filtered and concentrated in an evaporator, when the concentrated water extract of dried fruit reached the bottom of the vessel, the concentrate was fed into drier and dried under vacuum above 500 mm of mercury. Dried product (6 kg) was discharged from the bottom of the vessel, then pulverized and sieved through 30 mesh to obtain a powder of the water extract of dried fruits of *Emblica officinalis*.
The powder of a water extract of dried fruits of *Emblica officinalis* was found to have the following composition.
Polyphenol content: 60% (Titration method)
Hydrolysable gallo ellagic tannins: 20% (HPTLC method)

Example 7

Method of Manufacture of a Liquid Juice of Fruits of *Emblica officinalis*

Fresh fruits of *Emblica officinalis* 100 kgs was collected, and washed with water. The cleaned fruits were crushed in the screw expeller. The initial juice obtained on the tray of the screw expeller was collected in the feed tank under room temperature of 27° C. The initial juice was centrifuged to obtain filtrate which was collected and the residue which was removed. The collected filtrate was clarified in a rotating disc type clarifier (RPM-18000) to obtain final filtrate and some residue. After removing the residue, the final filtrate (clarified liquid juice of fruits of *Emblica officinalis*) was collected with a yield 60-70% of fruits of *Emblica officinalis* with total dissolved solids (TDS) 4-7%.
The liquid juice of fruits of *Emblica officinalis* was found to have the following composition.
Polyphenol content 12% (Titration method)
Hydrolysable gallo ellagic tannins: 5% (HPTLC method)

Example 8

Method of Manufacture of Powder of a Pectinase Treated Water Extract of Fruits of *Emblica officinalis*

Pectinase treated water extract of fruits of *Emblica officinalis* was prepared by pulping fruits of *Emblica officinalis* 100 kg with demineralized water to create slurry. The slurry was treated with pectinase and then filtered to obtain a solution. The solution was concentrated and dried under vacuum. Dried product (5 kg) was pulverized and sieved through 30 mesh to obtain a powder of a pectinase treated water extract of fruits of *Emblica officinalis*.
The powder of pectinase treated water extract of fruits of *Emblica officinalis* was found to have the following composition.
Polyphenol content: 64% (Titration method)
Hydrolysable gallo ellagic tannins: 22% (HPTLC)

Example 9

Method of Manufacture of Placebo Capsules 10 kgs of raw rice was washed well and roasted in a rotatory paddle type roaster. The roasted rice (9.5 kg) was powdered and sterilized under controlled temperature which was passed through 30 mesh sieve to obtain fine powder of roasted rice.
A 500 mg placebo capsule containing 500 mg of a powder of roasted rice is prepared by encapsulating the powder in hard gelatin capsules. The process is performed in an air-conditioned at 21° C. and de-humidified room. 2 kg of powder is charged into the hopper of a semi-automatic capsule filling machine. '0' size hard gelatin capsule shell is loaded to the tray and the extract powder is filled into the shell. The filled weight of capsules are checked simultaneously and these capsules are sorted by a sorting machine and polished with the help of a polishing machine to give 4000 placebo capsules of 500 mg each.
A 250 mg capsule containing 250 mg powder of roasted rice can be prepared by encapsulating the powder in hard gelatin capsules. The process is performed in an air-conditioned at 21° C. and de-humidified room. 2 kg of powder is charged into the hopper of a semi-automatic capsule filling machine. '2' size hard gelatin capsule shell is loaded to the tray and the extract powder is filled into the shell. The filled weight of capsules are checked simultaneously and these capsules are sorted by a sorting machine and polished with the help of a polishing machine to give 8000 placebo capsules of 250 mg each.

Example 10

Method of Treating Patients with Low Levels of HDL-C

Different extracts of fruits of *Emblica officinalis* were studied on normal humans for a period of 4 months. A total of 27 subjects were divided into 9 groups of 3 subjects each. Both male and female patients of age between 35 and 65 years, having HDL-C below 40 mg/dL were selected for the study. Those subjects on cholesterol lowering drugs, diabetic subjects with history of cardiovascular, thyroid, hepatic and renal diseases were excluded from the study. The subjects were given one 500 mg capsule of extract of fruits of *Emblica officinalis* or placebo at night after food with water for 4 months. The results are given below in table: 1.

TABLE 1

| Type of extract | Dose given | HDL-C in mg/dL (base line) | HDL-C in mg/dL (after treatment) | % change from baseline |
|---|---|---|---|---|
| Powder of juice of *Emblica officinalis* Group: A | 500 mg cap at night after food | 35 | 42 | +20% |
| Powder of Alcoholic extract of *Emblica officinalis* Group: B | 500 mg cap at night after food | 37 | 44 | +18.9% |
| Powder of Hydro alcoholic Extract of *Emblica officinalis* Group: C | 500 mg cap at night after food | 36 | 42 | +16.67% |
| Powder of Dried fruit of *Emblica officinalis* Group: D | 500 mg cap at night after food | 35 | 38 | +8.57% |
| Powder of Water extract of *Emblica officinalis* Group: E | 500 mg cap at night after food | 38 | 44 | +15.8% |
| Powder of Water extract of dried fruits of *Emblica officinalis* Group: F | 500 mg cap at night after food | 37 | 43 | +16.22% |
| Powder of Water extract of *Emblica officinalis* treated with pectinase Group: G | 500 mg cap at night after food | 34 | 39 | +14.71% |
| 10 ml Liquid juice of fruits of *Emblica officinalis* Group: H | 10 ml at night after food | 34 | 37 | +8.82% |
| Placebo Group: I | 500 mg cap at night after food | 36 | 35 | −2.78% |

The study shows that supplementation of extract of fruits of *Emblica officinalis* significantly increases the levels of HDL-C in subjects compared to Placebo.

Example 11

Method of Treating Patients with Low Levels of HDL-C and Memory Loss

Subjects both male and female in the age group of 50-75 years having a HDL-C of <40 mg/dl were screened for the study. Short term verbal memory was assessed with a 20-word free recall test. Participants were presented a list of 20, 1- or 2-syllable words at 2-second intervals and were then asked to recall in writing as many of the words in any order and had 2 minutes to do so. Memory deficit corresponds to a recall of up to 4 words out of 20 words. Those subjects who could recall only 4 or less words were selected for the study. Twenty seven subjects thus selected were given 250 mg capsules of extract of *Emblica officinalis* twice daily.

Group A: Subjects were given 250 mg capsules twice daily. The capsules contained powder of an alcoholic extract of fruits of *Emblica officinalis* prepared as described in Example 1

Group B: Subjects were given 250 mg capsules twice daily. The capsules contained powder of a water extract of fruits of *Emblica officinalis* prepared as described in Example 3

Group C: Subjects were given 250 mg capsules twice daily. The capsules contained powder of a hydroalcoholic extract of fruits of *Emblica officinalis* prepared as described in Example 2

Group D: Subjects were given 250 mg capsules twice daily. The capsules contained powder of a juice of fruits of *Emblica officinalis* prepared as described in Example 4.

Group E: Subjects were given 250 mg capsules twice daily. The capsules contained powder of dried fruits of *Emblica officinalis* prepared as described in Example 5.

Group F: Subjects were given 250 mg capsules twice daily. The capsules contained powder of water extract of dried fruits of *Emblica officinalis* prepared as described in Example 6.

Group G: Subjects were given 10 ml of liquid juice twice daily. The liquid juice of fruits of *Emblica officinalis* prepared as described in Example 7.

Group H: Subjects were given 250 mg capsules twice daily. The capsules contained powder of a pectinase treated water extract of fruits of *Emblica officinalis* prepared as described in Example 8.

Group I: Subjects were given 250 mg capsules twice daily. The capsules contained roasted rice powder prepared as described in Example 9.

250 mg capsules were given to the volunteers twice daily in the morning and night after food with water for 6 months.

Study assessments were made at baseline, 3 months and 6 months duration. The assessments include lipid profile and 20 word recall test. Table 2 gives the results of the study.

TABLE 2

| Patient No: | | Baseline 0 month | 3 months | Study End 6 months | % change from baseline to 6 months |
|---|---|---|---|---|---|
| Powder of alcoholic extract of *Emblica officinalis* Group: A | HDL | 34 mg/dL | 38 mg/dL | 42 mg/dL | +23.5% |
| | 20 word recall test score | 4/20 | 5/20 | 8/20 | +20% |
| Powder of water extract of *Emblica officinails* Group: B | HDL | 35 mg/dL | 38 mg/dL | 44 mg/dL | +25.7% |
| | 20 word recall test score | 3/20 | 5/20 | 9/20 | +30% |

TABLE 2-continued

| Patient No: | | Baseline 0 month | 3 months | Study End 6 months | % change from baseline to 6 months |
|---|---|---|---|---|---|
| Powder of hydroalcoholic extract of *Emblica officinalis* Group: C | HDL 20 word recall test score | 39 mg/dL 4/20 | 43 mg/dL 5/20 | 48 mg/dL 7/20 | +23% +15% |
| Powder of juice of *Emblica officinalis* Group: D | HDL 20 word recall test score | 33 mg/dL 3/20 | 36 mg/dL 4/20 | 41 mg/dL 7/20 | +24.2% +20% |
| Powder of dried fruit of *Emblica officinalis* Group: E | HDL 20 word recall test score | 40 mg/dL 4/20 | 41 mg/dL 5/20 | 44 mg/dL 8/20 | +10% +20% |
| Powder of water extract of dried fruits of *Emblica officinalis* Group: F | HDL 20 word recall test score | 35 mg/dL 4/20 | 39 mg/dL 4/20 | 41 mg/dL 6/20 | +17.1% +10% |
| 10 ml Liquid juice of fruits of *Emblica officinalis* Group: G | HDL 20 word recall test score | 37 mg/dL 4/20 | 39 mg/dL 5/20 | 41 mg/dL 7/20 | +10.8% +15% |
| Powder of water extract of dried fruits of *Emblica officinalis* treated with pectinase Group: H | HDL 20 word recall test score | 36 mg/dL 3/20 | 40 mg/dL 5/20 | 43 mg/dL 8/20 | +19.4% +25% |
| Placebo Group: I | HDL 20 word recall test score | 37 4/20 | 37 4/20 | 36 3/20 | −2.7% −5% |

All the subjects at the end of 6 months benefited from the supplementation of extracts of *Emblica officinalis* twice daily. The HDL-C value of all the subjects increased and there was also improvement in the word recall test score indicating a beneficial effect on memory enhancement. The changes were appreciable even at 3 months. All patients treated with extract of *Emblica officinalis* and the care givers approved of the general well being and rejuvenation experienced by the patients.

Example 12

Method of Treatment of Patients with Low Levels of HDL-C, Memory Loss and Cognitive Impairment with Extracts of Fresh Fruits of *Emblica officinalis*

Both male and female patients, aged 45 years or older, were eligible for the study if their HDL-C is <40 mg/dl and have memory loss documented by a Mini-Mental State Examination (MMSE) score (57), in the range 10 to 26 and 6 Item Cognitive Impairment Test (6CIT) score (58), of more than 8. Patients also weighed between 50 and 80 kg and had a stable medical condition for 3 months prior to screening, and an absence of clinically significant focal lesion on CT scan.

Patients were ineligible if they were on treatment with antidepressants, tranquilizers, mood stabilizers etc which would interfere with the study assessments. The objectives and implications of the study were explained to the patients and their care givers. The eligible patients were screened for the lipid profile and assessed with MMSE and 6 CIT for memory loss.

MMSE is one of the most commonly used tools to assess memory, concentration, and other cognitive skills. It is a research-based set of questions that provides a score about a person's general level of impairment. The MMSE has questions that assess five areas: orientation, short term memory (retention), attention, short term memory (recall) and language. The maximum score on MMSE is 30. A score of 24-30 is considered a normal range and a score below it is indicative of dementia. The 6CIT is a useful dementia screening tool in Primary Care. The 6CIT uses an inverse score and questions are weighted to produce a total score out of 28. Scores of 0-7 are considered normal and 8 or more are considered significant. The test has high sensitivity without compromising specificity even in mild dementia.

The 15 subjects who fulfilled the study criteria were enrolled into 5 groups of 3 each in the study. 250 mg capsules were given twice daily: once in the morning and once at night after food with water for 6 months.

Group A: Subjects were given 250 mg capsules of a powder of an alcoholic extract of fruits of *Emblica officinalis* twice daily for 6 months. The extract was prepared as described in Example 1

Group B: Subjects were given 250 mg capsules of powder of a water extract of fruits of *Emblica officinalis* twice daily for 6 months. The extract was prepared as described in Example 3

Group C: Subjects were given 250 mg capsules of a powder of a hydroalcoholic extract of fruits of *Emblica officinalis* twice daily for 6 months. The extract was prepared as described in Example 2

Group D: Subjects were given 250 mg capsules of a powder of a pectinase treated water extract of fruits of *Emblica officinalis* twice daily for 6 months. The extract was prepared as described in Example 8

Group E: Subjects were given 250 mg capsules of a powder of water extract of dried fruits of *Emblica officinalis* twice daily for 6 months. The extract was prepared as described in Example 6

The study assessments were made at baseline, 3 months and 6 months duration. The assessments included lipid profile. MMSE and 6 CIT scoring. Results of the study are provided in Table 3 below.

TABLE 3

| Patient No: | | Baseline 0 month | 3 months | Study End 6 months | % change from baseline to 6 months |
|---|---|---|---|---|---|
| Powder of alcoholic extract of *Emblica officinalis* Group: A | HDL MMSE 6CIT | 35 mg/dL 20/30 14/28 | 40 mg/dL 21/30 12/28 | 43 mg/dL 23/30 10/28 | +22.8% +10% +14% |
| Powder of water extract of *Emblica officinalis* Group: B | HDL MMSE 6CIT | 33 mg/dL 16/30 14/28 | 38 mg/dL 19/30 12/28 | 41 mg/dL 22/30 8/28 | +24.2% +20% +21.4% |
| Powder of hydroalcoholic extract of *Emblica officinalis* Group: C | HDL MMSE 6CIT | 36 mg/dL 22/30 12/28 | 41 mg/dL 23/30 12/28 | 44 mg/dL 26/30 10/28 | +22.2% +13% +7% |
| Powder of water extract of *Emblica officinalis* treated with pectinase Group: D | HDL MMSE 6CIT | 35 mg/dL 18/30 10/28 | 39 mg/dL 20/30 8/28 | 42 mg/dL 21/30 6/28 | +20% +10% +14% |
| Powder of a water extract of dried fruits of *Emblica offficinalis*, Group: E | HDL MMSE 6CIT | 35 20/30 11/28 | 38 22/30 10/28 | 41 23/30 8/28 | +17.1% +10% +10.7% |

As seen in Table 3, at the end of study all subjects performed better with MMSE and 6CIT, showing that administration of extract of *Emblica officinalis* as 250 mg capsules twice daily significantly improved dementia by enhancing the memory and cognitive ability along with the elevation of HDL-C.

Example 13

Method of Treatment of Patients with Alzheimer's Disease with Extracts of Fresh Fruits of *Emblica officinalis*

Patients aged between 60 and 80 years of either sex with HDL-C less than 40 mg/dL with a history of gradual and progressive cognitive decline for at least six months, diagnosis of probable Alzheimer's disease according to the criteria of National Institute of Neurological and Communicative Disorders and Stroke and Alzheimer's Disease and Related Disorders Association (NINCDS/ADRDA) and presence of mild to moderate dementia (score of >12 on the cognitive subscale of Alzheimer's disease assessment scale (ADAS-cog) (59) were selected for the study. Patients were excluded if they are having any significant systemic diseases, psychiatric illness or any drugs affecting the cognitive functions.

ADAS-cog is a subscale of 11 items that evaluates selected aspects of attention, language, memory, orientation, praxis, and reasoning. Scores for ADAS-cog range from 0 to 70 (very severe).

The study subjects were given 250 mg capsules of extract of *Emblica officinalis* twice daily for 6 months. A total of 27 subjects were selected for the study. They were divided into 9 groups of 3 subjects each.

Group I: Subjects were given 250 mg capsules twice daily. The capsules contained powder of an alcoholic extract of fruits of *Emblica officinalis* prepared as described in Example 1

Group II: Subjects were given 250 mg capsules twice daily. The capsules contained powder of a water extract of fruits of *Emblica officinalis* prepared as described in Example 3

Group III: Subjects were given 250 mg capsules twice daily. The capsules contained powder of a hydroalcoholic extract of fruits of *Emblica officinalis* prepared as described in Example 2

Group IV: Subjects were given 250 mg capsules twice daily. The capsules contained powder of water extract of dried fruits of *Emblica officinalis* prepared as described in Example 6.

Group V: Subjects were given 250 mg capsules twice daily. The capsules contained powder of a pectinase treated water extract of fruits of *Emblica officinalis* prepared as described in Example 8.

Group VI: Subjects were given 250 mg capsules twice daily. The capsules contained powder of dried fruits of *Emblica officinalis* prepared as described in Example 5.

Group VII: Subjects were given 10 ml of liquid juice twice daily. The liquid juice of fruits of *Emblica officinalis* prepared as described in Example 7.

Group VIII: Subjects were given 250 mg capsules twice daily. The capsules contained powder of a juice of fruits of *Emblica officinalis* prepared as described in Example 4.

Group IX: Subjects were given 250 mg capsules twice daily. The capsules contained roasted rice powder prepared as described in Example 9.

The study visits were done at baseline, 3 months and 6 months. The results are provided in Table 4.

TABLE 4

| Groups | | | Baseline (0 month) | 3 months | Study End 6 months | % change from baseline to 6 months |
|---|---|---|---|---|---|---|
| Group I | Powder of alcoholic extract *Emblica* | ADAS-cog score | 26 | 24 | 18 | +30.7% |
| | | HDL-C | 38 | 42 | 46 | +21% |

TABLE 4-continued

| Groups | | | Baseline (0 month) | 3 months | Study End 6 months | % change from baseline to 6 months |
|---|---|---|---|---|---|---|
| | officinalis 250 mg | | | | | |
| Group II | Powder of water extract of Emblica officinalis 250 mg | ADAS-cog score | 27 | 24 | 19 | +29.6% |
| | | HDL-C | 33 | 37 | 39 | +18% |
| Group III | Powder of hydroalcoholic extract of Emblica officinalis 250 mg | ADAS-cog score | 26 | 24 | 20 | +23% |
| | | HDL-C | 35 | 38 | 41 | +17% |
| Group IV | Powder of water extract of dried fruits of Emblica officinalis 250 mg | ADAS-cog score | 28 | 25 | 21 | +25% |
| | | HDL-C | 34 | 37 | 40 | +17.6% |
| Group V | Powder of a pectinase treated water extract of Emblica officinalis 250 mg | ADAS-cog score | 26 | 23 | 19 | +26.9% |
| | | HDL-C | 38 | 41 | 45 | +18% |
| Group VI | Powder of dried fruits of Emblica officinalis 250 mg | ADAS-cog score | 27 | 26 | 23 | +14.8% |
| | | HDL-C | 35 | 38 | 42 | +20% |
| Group VII | Liquid juice of fruits of Emblica officinalis 10 ml | ADAS-cog score | 26 | 24 | 22 | +15% |
| | | HDL-C | 38 | 41 | 45 | +18% |
| Group VIII | Powder of a juice of fruits of Emblica officinalis 250 mg | ADAS-cog score | 25 | 22 | 20 | +20% |
| | | HDL-C | 36 | 40 | 42 | +16.6% |
| Group IX | Placebo capsule 250 mg | ADAS-cog score | 26 | 28 | 32 | +23% |
| | | HDL-C | 38 | 36 | 35 | +7.8% |

As seen in Table 4, there were no significant differences between the groups at baseline (week 0) on the ADAS-cog rating scale. In groups given different extracts of *Emblica officinalis* there were significant change on the ADAS-cog rating scale scores compared to placebo. The improvement in the ADAS-cog score was significant over a period of 6 months, which was seen even at 3 months of treatment. This study showed that patients with mild to moderate Alzheimer's disease receiving an extract *Emblica officinalis* experienced significant benefits in cognition with 6 months of treatment. The extract of fruits of *Emblica officinalis* may offer an effective method of treating patients with dementia and Alzheimer's disease and for slowing the progress of Alzheimer's disease.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

REFERENCES

1. Kral V A, Neuro-psychiatric observations in an old peoples home: studies of memory dysfunction in senescence, J Gerontol, 13:169-176 (1958)
2. Petersen R C, Smith G, Kokmen E, Ivnik R J, Tangalos E G, Memory function in normal aging, Neurology, 42:396-401 (1992)
3. Youngjohn J R, Crook T H III, Learning, forgetting, and retrieval of everyday material across the adult life span, J Clin Exp Neuropsychol, 15:447-460 (1993)
4. Mitrushina M, Satz P, Changes in cognitive functioning associated with normal Aging, Arch Clin Neuropsychol, 6:49-60 (1991)
5. Small S A, Stern Y, Tang M, Mayeux R, Selective decline in memory function among healthy elderly, Neurology, 52:1392-1396 (1999).
6. Craik F I M, McDowd J M, Age differences in recall and recognition, J Exp Psychol Learn Mem Cogn, 13:474-479 (1987).

7. Zelinski E M, Gilewski M J, Schaie K W, Individual differences in cross-sectional and 3-year longitudinal memory performance across the adult life span, Psychol Aging, 8:176-186 (1993).
8. Rubin E H, Storandt M, Miller J P, et al. A prospective study of cognitive function and onset of dementia in cognitively healthy elders, Arch Neurol, 55:395-401 (1998).
9. Hanninen T, Koivisto K, Reinikainen K J, et al. Prevalence of ageing-associated cognitive decline in an elderly population, Age Ageing, 25:201-205 (1996).
10. Rapp P R, Amaral D G, Individual differences in the cognitive and neurobiological consequences of normal aging, Trends Neurosci, 15:340-345 (1992).
11. Diehl M, Willis S L, Schaie K W, et al. Everyday problem solving in older adults: observational assessment and cognitive correlates, Psychol Aging, 10: 478-491 (1995).
12. Hultsch D F, Hammer M, Small B J, Age differences in cognitive performance in later life: relationships to self-reported health and activity life style, J Gerontol, 48:1-11 (1993).
13. Albert S A, Michaels K, Padilla M, et al. Functional significance of mild cognitive impairment in elderly patients without a dementia diagnosis, Am J Geriatr Psychiatry, 7:213-220 (1999).
14. Braak H, Braak E, Evolution of the neuropathology of Alzheimer's disease, Acta Neurol Scand Suppl, 165:3-12 (1996).
15. Masur D M, Sliwinski M, Lipton R B, Blau A D, Crystal H A, Neuropsychological prediction of dementia and the absence of dementia in healthy elderly persons, Neurology, 44:1427-1432 (1994)
16. Jacobs D M, Sano M, Dooneief G, Marder K, Bell K L, Stern Y, Neuropsychological detection and characterization of preclinical Alzheimer's disease, Neurology, 45:957-962 (1995).
17. Small G W, Rabins P V, Barry P P, et al. Diagnosis and treatment of Alzheimer disease and related disorders, Consensus statement of the American Association for Geriatric Psychiatry, the Alzheimer's Association, and the American Geriatrics Society, JAMA 278:1363-71 (1997).
18. Morris J C, Dementia update 2005, Alzheimer Dis Assoc Disord, 19:100-17 (2005).
19. Tschanz J T, Corcoran C, Skoog I, et al. Dementia: the leading predictor of death in a defined elderly population: the Cache County Study, Neurology, 62:1156-62 (2004).
20. Jurevies H, Morell P, Cholesterol for synthesis of myelin is made locally, not imported into brain, J Neurochem, 64: 895-901 (1995).
21. Michikawa M, Cholesterol paradox: is high total or low HDL cholesterol level a risk for Alzheimer's disease? J Neurosci Res, 72:141-6 (2003).
22. Koudinov A R, Koudinova N V, Essential role for cholesterol in synaptic plasticity and neuronal degeneration, FASEB J, 15:1858-60 (2001).
23. Mauch D H, Nagler K, Schumacher S, et al. CNS synaptogenesis promoted by glia-derived cholesterol, Science, 294:1354-7 (2001).
24. Fan Q W, Yu W, Senda T, et al. Cholesterol-dependent modulation of tau phosphorylation in cultured neurons, J Neurochem, 76:391-400 (2001).
25. Vetrivel K S, Cheng H, Lin W, et al. Association of gammasecretase with lipid rafts in post-Golgi and endosome membranes. J Biol Chem, 279:44945-54 (2004).
26. Koudinov A R, Berezov T T, Kumar A, et al. Alzheimer's amyloid beta interaction with normal human plasma high density lipoprotein: association with apolipoprotein and lipids, Clin Chim Acta, 270:75-84 (1998).
27. Refolo L M, Malester B, LaFrancois J, et al. Hypercholesterolemia accelerates the Alzheimer's amyloid pathology in a transgenic mouse model, Neurobiol Dis, 7:321-31 (2000).
28. Sparks D L, Scheff S W, Hunsaker J C 3rd, et al. Induction of Alzheimer-like beta-amyloid immunoreactivity in the brains of rabbits with dietary cholesterol, Exp Neurol, 126: 88-94 (1994).
29. Simons M, Keller P, De Strooper B, et al. Cholesterol depletion inhibits the generation of beta-amyloid in hippocampal neurons, Proc Natl Acad Sci USA, 95:6460-4 (1998).
30. Eckert G P, Kirsch C, Leutz S, et al. Cholesterol modulates amyloid beta-peptide's membrane interactions, Pharmacopsychiatry, 36(suppl 2):S136-43 (2003).
31. Cockerill G W, Huehns T Y, Weerasinghe A, et al. Elevation of plasma high-density lipoprotein concentration reduces interleukin-1-induced expression of E-selectin in an in vivo model of acute inflammation, Circulation, 103:108-12 (2001).
32. Paterno R, Ruocco A, Postiglione A, et al. Reconstituted highdensity lipoprotein exhibits neuroprotection in two rat models of stroke, Cerebrovasc Dis, 17:204-11 (2004).
33. van Exel E, de Craen A J, Gussekloo J, et al. Association between high-density lipoprotein and cognitive impairment in the oldest old. Ann Neurol, 51:716-21 (2002)
34. Wolf H, Hensel A, Arendt T, et al. Serum lipids and hippocampal volume: the link to Alzheimer's disease-?Ann Neurol, 56:745-8 (2004).
35. Bonarek M, Barberger-Gateau P, Letenneur L, et al. Relationships between cholesterol, apolipoprotein E polymorphism and dementia: a cross-sectional analysis from the PAQUID study, Neuroepidemiology, 19:141-8 (2000)
36. Merched A, Xia Y, Visvikis S, et al. Decreased high-density lipoprotein cholesterol and serum apolipoprotein AI concentrations are highly correlated with the severity of Alzheimer's disease, Neurobiol Aging, 21:27-30, (2000)
37. Notkola interleukin (IL), Sulkava R, Pekkanen J, Erkinjuntti T, Ehnholm C, Kivinen P, Tuomilehto J, Nissinen A, Serum total cholesterol, apolipoprotein E epsilon 4 allele, and Alzheimer's disease, *Neuroepidemiology,* 17:14-20 (1998).
38. Stewart R, White L R, Xue Q L, Launer L J, Twenty-six-year change in total cholesterol levels and incident dementia: the Honolulu-Asia Aging Study, *Arch Neurol,* 64:103-107 (2007).
39. Solomon A, Kareholt I, Ngandu T, Winblad B, Nissinen A, Tuomilehto J, Soininen H, Kivipelto M, Serum cholesterol changes after midlife and late-life cognition: twenty-one-year follow-up study, *Neurology,* 68:751-756 (2007).
40. Saczynski J S, White L, Peila R L, Rodriguez B L, Launer L J, The relation between apolipoprotein A-I and dementia: the Honolulu-Asia aging study, *Am J Epidemiol,* 165:985-992 (2007).
41. Yaffe K, Barrett-Connor E, Lin F, Grady D, Serum lipoprotein levels, statin use, and cognitive function in older women, *Arch Neurol,* 59:378-384 (2002).
42. Moroney J T, Tang M X, Berglund L, Small S, Merchant C, Bell K, Stern Y, Mayeux R, Low-density lipoprotein cholesterol and the risk of dementia with stroke, *JAMA,* 282:254-260 (1999)

43. Evans R M, Hui S, Perkins A, Lahiri D K, Poirier J, Farlow M R, Cholesterol and APOE genotype interact to influence Alzheimer disease progression, *Neurology*, 62:1869-1871 (2004).
44. Reitz C, Tang M X, Luchsinger J, Mayeux R, Relation of plasma lipids to Alzheimer disease and vascular dementia, *Arch Neurol*, 61: 705-714 (2004).
45. Razay G, Vreugdenhil A, Wilcock G, The metabolic syndrome and Alzheimer disease, *Arch Neurol*, 64:93-96 (2007)
46. Komulainen P, Lakka T A, Kivipelto M, Hassinen M, Helkala E L, Haapala I, Nissinen A, Rauramaa R, Metabolic syndrome and cognitive function: a population-based follow-up study in elderly women, *Dement Geriatr Cogn Disord*, 23:29-34 (2007).
47. Wolf H, Hensel A, Arendt T, Kivipelto M, Winblad B, Gertz H J, Serum lipids and hippocampal volume: the link to Alzheimer's disease? *Ann Neurol*, 56:745-748 (2004).
48. van E E, de Craen A J, Gussekloo J, Houx P. Bootsma-van der W A, Macfarlane P W, Blauw G J, Westendorp R G, Association between highdensity lipoprotein and cognitive impairment in the oldest old, *Ann Neurol*, 51:716-721 (2002).
49. Katzman R, Aronson M, Fuld P, Kawas C, Brown T, Morgenstern H, Frishman W, Gidez L, Eder H, Ooi W L, Development of dementing illnesses in an 80-year-old volunteer cohort, *Ann Neurol*, 25: 317-324 (1989).
50. Muckle T J, Roy J R, High-density lipoprotein cholesterol in differential diagnosis of senile dementia, *Lancet*, 1:1191-1193 (1985).
51. Michikawa M, Cholesterol paradox: is high total or low HDL cholesterol level a risk for Alzheimer's disease? *J Neurosci Res*, 72: 141-146 (2003).
52. Olesen O F, Dago L, High density lipoprotein inhibits assembly of amyloid beta-peptides into fibrils, *Biochem Biophys Res Commun*, 270:62-66 (2000).
53. Archana Singh-Manoux, David Gimeno, Mika Kivimaki, Eric Brunner and Michael G, Marmot, Low HDL Cholesterol Is a Risk Factor for Deficit and Decline in Memory in Midlife, The Whitehall II Study *Arterioscler Thromb Vase Biol*, p 1557-1563 (August 2008)
54. Effect standardized of amla extract on atherosclerosis and dyslipidemia, *Ind. J. Pharm. Sci*, 68 (4), 43.7-441, (2006)
55. Amlamax™ in the Management of Dyslipidemia in Humans *Ind J. Pharm. Sci*, 70(4):504-507, (2008)
56. A pilot clinical study to evaluate the effect of *emblica officinalis* extract (Amlamax™) on markers of systemic inflammation and dyslipidemia *Ind. J. Clin. Biochem*, 23(4):378-381 (2008)
57. Folstein M F, Folstein S E, McHugh P R, "Mini-mental state." A practical method for grading the cognitive state of patients for the clinician, J Psychiatr Res, 12:189-198 (1975)
58. Brooke P and Bullock R, Validation of a 6-item cognitive impairment test with a view to primary care usage, International J. Geriatric Psychiatry, 14 (II): 936-40 (1999).
59. Rosen W G, et al. *Am J Psychiatry*, 141:1356-1364 (1984).

I claim:

1. A method of treating a patient having Alzheimer's disease, comprising administering effective doses of an extract of fruits of *Emblica Officinalis* to the patient, whereby HDL cholesterol increases in the patient, wherein the extract is prepared by a method comprising: pulping fruits of *Emblica officinalis* with demineralized water to create a slurry; treating the slurry with pectinase; filtering the slurry to create a solution: and concentrating the solution to generate the extract of *Emblica officinalis*.

2. The method of claim 1, wherein the HDL cholesterol level in the patient is less than 40 mg/dl prior to administration of said effective doses of the extract of fruits.

3. The method of claim 1, wherein said administering the extract improves the ADAS-cog score in the patient by about 26% in about 6 months.

4. A method of treating a patient having dementia comprising administering effective doses of an extract of fruits of *Emblica Officinalis* to the patient, whereby HDL cholesterol increases in the patient, wherein the extract is prepared by a method comprising: pulping fruits of *Emblica officinalis* with demineralized water to create a slurry; treating the slurry with pectinase; filtering the slurry to create a solution; and concentrating the solution to generate the extract of *Emblica officinalis*.

5. The method of claim 1, wherein the HDL cholesterol level in the patient is less than 40 mg/dl prior to administration of said effective doses of the extract.

6. The method of claim 4, wherein MMSE score for the patient improves about 10% after 6 months of administering said effective doses of the extract.

7. The method of claim 4, wherein MMSE score for the patient improves about 18 to about 21 points after 6 months of administering said effective doses of the extract.

8. A method of treating memory loss in a patient having memory loss comprising administering effective doses of an extract of fruits of *Emblica Officinalis* to the patient, whereby HDL cholesterol increases in the patient, wherein the extract is prepared by a method comprising: pulping fruits of *Emblica officinalis* with demineralized water to create a slurry; treating the slurry with pectinase; filtering the slurry to create a solution; and concentrating the solution to generate the extract of *Emblica officinalis*.

9. The method of claim 8, wherein the HDL cholesterol level in the patient is less than 40 mg/dl prior to administration of said effective doses of the extract.

10. The method of treating memory loss of claim 8, wherein the patient improves by about 25% on a 20 word recall test following said administering the effective doses.

* * * * *